United States Patent

Wong et al.

[11] Patent Number: 5,910,321
[45] Date of Patent: Jun. 8, 1999

[54] MULTIPLE FLOW PATH DEVICE FOR ORAL DELIVERY OF DISCRETE UNITS

[75] Inventors: Patrick S.-L. Wong, Burlingame; Nathan Roth, San Francisco; Vincent J. Ferrari, Foster City, all of Calif.

[73] Assignee: Alza Corporation, Palo Alto, Calif.

[21] Appl. No.: 08/949,753

[22] Filed: Oct. 14, 1997

Related U.S. Application Data

[60] Provisional application No. 60/028,705, Oct. 18, 1996.
[51] Int. Cl.$^6$ ..................................................... A61K 9/24
[52] U.S. Cl. ........................... 424/473; 424/464; 424/468; 424/489; 604/83; 604/84
[58] Field of Search .................................. 424/464, 468, 424/473, 489; 604/83, 84; 222/476, 477, 478; 239/33

[56] References Cited

U.S. PATENT DOCUMENTS

| | | | |
|---|---|---|---|
| 1,661,400 | 3/1928 | Yehle . | |
| 2,436,505 | 2/1948 | DuRall | 128/222 |
| 2,867,536 | 1/1959 | Mead et al. | 99/138 |
| 3,409,224 | 11/1968 | Harp et al. | 239/33 |
| 3,610,483 | 10/1971 | Visconti | 222/478 |
| 3,845,770 | 11/1974 | Theeuwes et al. | 128/260 |
| 3,995,631 | 12/1976 | Higuchi et al. | 128/260 |
| 4,034,756 | 7/1977 | Higuchi et al. | 128/260 |
| 4,111,202 | 9/1978 | Theeuwes | 128/260 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,581,013 | 4/1986 | Allen | 604/78 |
| 4,765,989 | 8/1988 | Wong et al. | 424/473 |
| 4,792,333 | 12/1988 | Kidder | 604/83 |
| 4,981,468 | 1/1991 | Benefiel et al. | 604/83 |
| 5,094,861 | 3/1992 | D'Auguste et al. | 426/85 |
| 5,123,915 | 6/1992 | Miller et al. | 606/234 |
| 5,222,940 | 6/1993 | Wilk | 604/77 |
| 5,223,259 | 6/1993 | Lackney | 424/435 |
| 5,509,605 | 4/1996 | Cripe | 239/33 |
| 5,718,681 | 2/1998 | Manning | 604/56 |
| 5,780,058 | 7/1998 | Wong et al. | 424/473 |

FOREIGN PATENT DOCUMENTS

| | | |
|---|---|---|
| 1906964 | 2/1969 | Germany . |
| WO97/03634 | 2/1997 | WIPO . |

*Primary Examiner*—Thurman K. Page
*Assistant Examiner*—Lakshmi Channavajjala
*Attorney, Agent, or Firm*—Andrea G. Reister; Howrey & Simon

[57] ABSTRACT

The present invention is directed to an oral active agent delivery system and method for delivering discrete units of an active agent to a patient. An elongate tubular member having first and second ends comprises first and second flow paths. Either or both of said flow paths contains an active agent. Liquid is drawn up into the first end of the member, and the liquid and active agent is drawn out of the second end of the member and into the patient's mouth.

21 Claims, 4 Drawing Sheets

5,910,321

MULTIPLE FLOW PATH DEVICE FOR ORAL DELIVERY OF DISCRETE UNITS

This application claims the benefit of U.S. Provisional Application No. 60/028,705, filed Oct. 18, 1996.

FIELD OF THE INVENTION

The present invention is related to the oral delivery of an active agent. More particularly, it is a device and method for oral delivery of an active agent from a plurality of flow paths, at least one of which contains a suspended active agent.

BACKGROUND OF THE INVENTION

Tablets, capsules, caplets and many other types of devices have been used for oral delivery of active agents. These forms are relatively easy to manufacture and convenient for use in the hospital or other institutional settings or at home. Many different types of active agents have been incorporated into such dosage forms—ranging from analgesics to antibiotics to hormones.

There are patients that, because of age or infirmity, have difficulty swallowing solid oral dosage forms. According to Kikendall et al., *Digestive Diseases and Sciences* 28:2 (1983), there were 221 cases documented between 1970–1982 of tablet and capsule induced esophageal injury. The most commonly implicated drugs were tetracycline (108 cases), emepronium bromide (36 cases), potassium chloride (16 cases) and ferrous salts (12 cases).

In view of the above, various approaches have been proposed whereby swallowing of a large solid system is avoided as is described in the following patents and applications which are all incorporated by reference herein.

U.S. Pat. No. 2,436,505 to DuRall describes a pill doser for administering medicines in liquid form or in pills or tablets. The device has a bowl at the top for containing the medicine and a tube that can be submerged in a liquid held in a drinking glass. The liquid is drawn upward for administering the liquid and any pill or tablet present in the bowl.

U.S. Pat. No. 2,867,536 to Mead et al. describes an improved drinking straw where a soluble flavoring material is contained within an annular space contained within an inner and an outer tube. The inner tube has a bore through which liquid can be drawn. During use, the upper and lower caps are removed, the flavoring material is emptied into the liquid and the flavored liquid is drawn up through the inner tube and into the mouth.

U.S. Pat. No. 3,610,483 to Visconti describes a dispensing device for liquid medication that is formed in the shape of a straw. A predetermined dose of liquid medication is loaded into the straw which is then capped at both ends until the medication is dispensed when a patient removes the caps and sucks air into the device.

U.S. Pat. No. 4,581,013 to Allen is directed to a doser for orally administering a medication. A tube with a removable closure and a radially extending plate supports a solid medication and permits passage of a stream of liquid. The tube is fitted on top of a straw that is placed into a liquid.

U.S. Pat. No. 4,792,333 to Kidder describes a tamper proof package for containing and orally administering a solid substance. A tube has two portions that are separated by a supporting and confining means that supports and confines the solid substance but permits fluid flow. The ends of the tube are hermetically sealed.

U.S. Pat. No. 4,981,468 to Benefiel et al. is directed to a unit dosage form for delivering a therapeutic agent in free-flowing form. A slanted grid supports the dose between two ends of a tube.

PCT Patent Application No. PCT/US96/11812 describes an oral active agent delivery system comprising a hollow chamber that contains discrete units of active agent. A fluid passing retainer prevents release of the discrete units but permits fluid entry into the chamber. The retainer is transportable with the fluid entering the system.

A variety of other oral delivery systems have been described. These include a medicated pacifier (U.S. Pat. No. 5,123,915 to Miller et al.) and a lollipop type device for delivery of a solid medicament (U.S. Pat. No. 5,223,259 to Lackney). None of these devices or the devices described previously provide for the delivery of a solid medicament into the oral cavity as a large bolus dose, while avoiding the difficulties inherent in swallowing a solid system such as a tablet or a capsule or the shelf-life problems encountered when a medicine is dissolved or dispersed in a fluid.

SUMMARY OF THE INVENTION

Accordingly, in one aspect, the present invention is directed to a device for administering discrete units of an active agent formulation in combination with a fluid. The device comprises an elongate tubular member having a first end and a second end. The tubular member comprises a first and a second flow path. Either or both of the flow paths contains a therapeutically effective amount of an active agent in the form of discrete units.

In a second aspect, the present invention is directed to a method for delivering discrete units of an active agent in combination with a fluid to a patient. The method comprises entraining discrete units of active agent in a fluid and introducing the fluid into the mouth of a patient. The method further involves simultaneously introducing a supplemental stream of fluid into the mouth of the patient.

DESCRIPTION OF THE DRAWINGS

The figures are not drawn to scale, but are set forth to illustrate various embodiments of the invention. Like numbers refer to like structures.

DETAILED DESCRIPTION OF THE INVENTION

The present invention provides a device that is useful for the oral delivery of an active agent in the form of discrete units suspended in a fluid stream. The invention also provides a method for the delivery of the discrete units in a convenient form.

Definitions

The term "discrete units" intends the active agent in solid or particulate form.

The term "oral dosage form" means that the active agent is placed in a discrete unit that is delivered orally and is capable of maintaining its physical configuration and chemical integrity while housed within the delivery device.

The term "therapeutically effective amount" means the amount of the active agent needed to effect the desired pharmacologic, often beneficial, result.

The term "fluid passing active agent retainer" means a valve, plug, grid, restriction or the like that allows for passage of fluid but does not allow for passage of other ingredients such as the active agent that is contained in the delivery device.

The dispensing devices of the invention find use where it is inconvenient or unsafe to use oral dosage forms such as capsules or tablets. The devices may be particularly useful in geriatric or pediatric patient populations but they may also be useful for those who have difficulty swallowing capsules or tablets. A single delivery device or several devices can be administered to a patient during a therapeutic program.

We have found that in order to permit suspended drug particles to be easily swallowed, a relatively large volume of fluid should flow into the mouth. However, when a single lumen device is used, as described in PCT/US96/11812, and the lumen containing the drug is sized to allow for the flow of this volume, the velocity of flow tends to drop to a level where the particles are not rapidly, uniformly and completely entrained in the fluid stream flowing inter the users mouth. We have found that flow velocities and flow volume can both be maintained at desirable levels if the required volume of fluid needed to facilitate swallowing is obtained from a plurality of smaller cross-section flow paths, one of more of which contain the drug, rather than from one larger cross-section path.

Figure 1A:
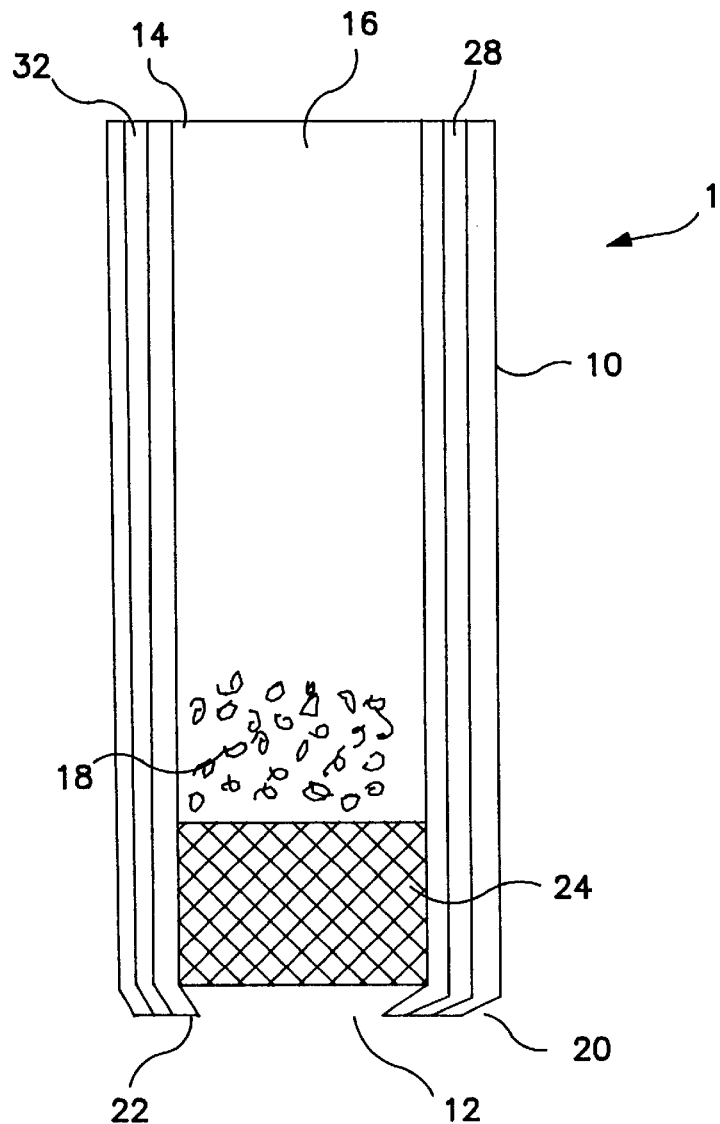
FIG. 1A is a side view of one embodiment of the delivery system of the invention.
Figure 1B:
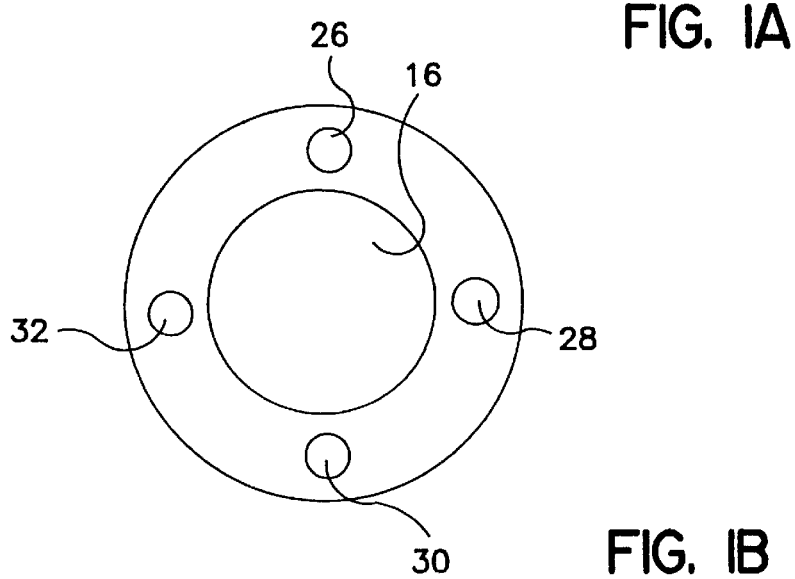
FIG. 1B is a top view of the first end of the system of FIG. 1A.

FIG. 1A depicts, in a side view, one embodiment of the delivery device according to the invention prior to placement in a drinkable fluid. Dispensing device 1 is shown in FIG. 1A to comprise an elongate tubular member 10 with a first end 12 and a second end 14. Contained within tubular member 10 is a first lumen 16 that contains an active agent 18 and a fluid passing active agent retainer 20. The fluid passing active agent retainer 20 comprises a restriction 22 and a plug 24. The restriction 22 is formed by crimping the end of tubular member 10. The inner diameter of the restriction 22 is smaller than the outside diameter of the plug 24 such that the active agent 18 and plug 24 are retained within the tubular member 10 but plug 24 can slide upwardly in lumen 16 as fluid is drawn therethrough. Also contained within the tubular member are lumens 26, 28, 30 and 32 (see FIG. 1B). These lumens may or may not contain an active agent, which active agent may be the same as or different from the active agent 18 retained within the first lumen 16. In the embodiment shown in FIGS. 1A and 1B, lumens 26, 28, 30 and 32 contain no active agent. When in use, the first end 12 of the device 1 is placed in a fluid and the second end 14 is placed in the mouth of a patient. The patient begins to suck and fluid is drawn up through lumen 16, 26, 28, 30 and 32 (the flow paths). The discrete units are entrained in the fluid drawn through lumen 16. Supplemental streams of fluid are drawn up through the other lumens. In this way, a large dose of active agent 18, contained within lumen 16 is suspended in a lower volume, higher velocity stream and is mixed in the patients mouth with the fluid drawn through lumens 26, 28, 30 and 32, to provide the fluid volume needed so it can easily be swallowed.

Figure 2A:
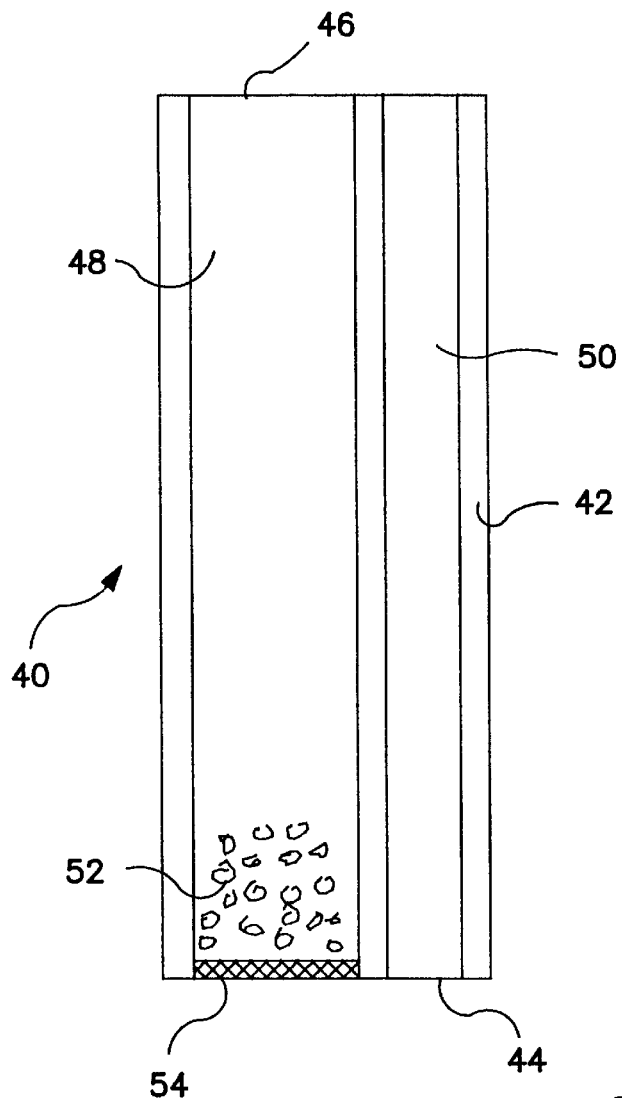
FIG. 2A is a side view of a second embodiment of the delivery system of the invention.
Figure 2B:
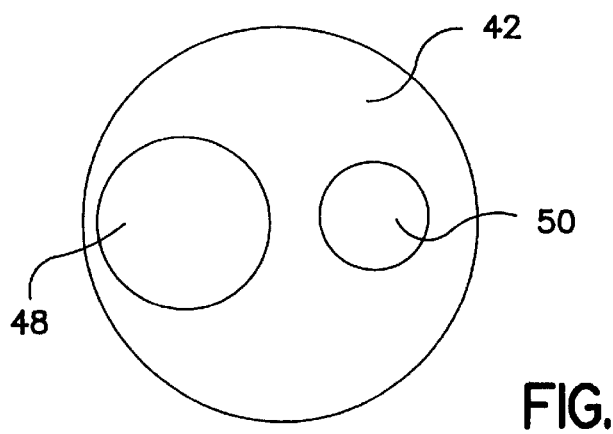
FIG. 2B is a top view of the first end of the system of FIG. 2A.

FIG. 2A is a side view of a second embodiment of the device of the invention. The device is in prepared form prior to placement in a fluid. Dispensing device 40 is shown in FIG. 2A to comprise an elongate tubular member 42 with a first end 44 and a second end 46. Contained within tubular member 42 is a first lumen 48 and a second lumen 50 (see also FIG. 2B). FIG. 2A shows the active agent 18 contained within the first lumen 48, but the active agent may be contained in either or both of the lumens. Further shown in FIG. 2A is fluid passing active agent retainer 54. In this case, retainer 54 comprises a grid whose openings are smaller than the discrete units of active agent such that liquid may pass through the grid, but the active agent will remain inside the lumen until fluid is drawn up through the grid and the active agent and into the mouth. When in use, the first end 44 of the member 42 is inserted into a fluid and the second end 46 is placed into the mouth of a patient. The patient begins to suck and fluid is drawn up through lumens 48 and 50. A large dose of active agent (e.g. up to 5000 mg) can be administered because sufficient fluid will be drawn through both lumens to enable easy swallowing.

Figure 3:
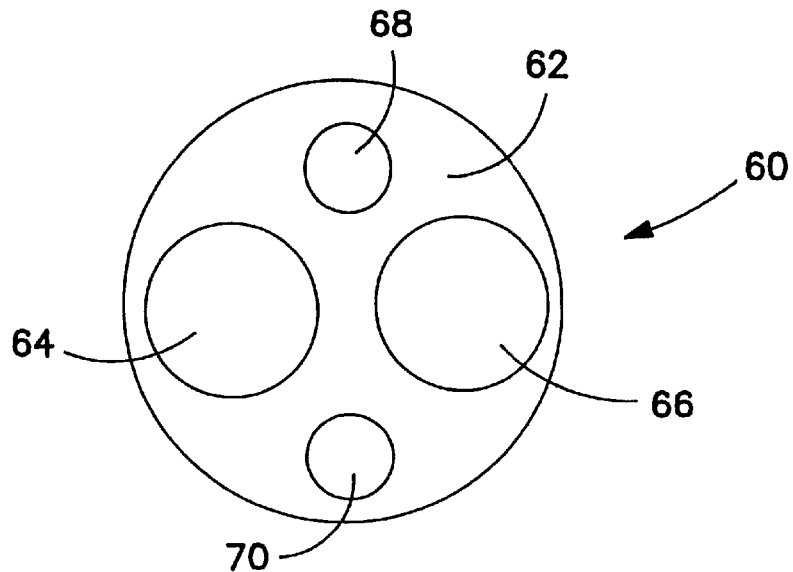
FIGS. 3, 4, 5, 6 and 7 are top views of other embodiments according to the invention.
Figure 4:
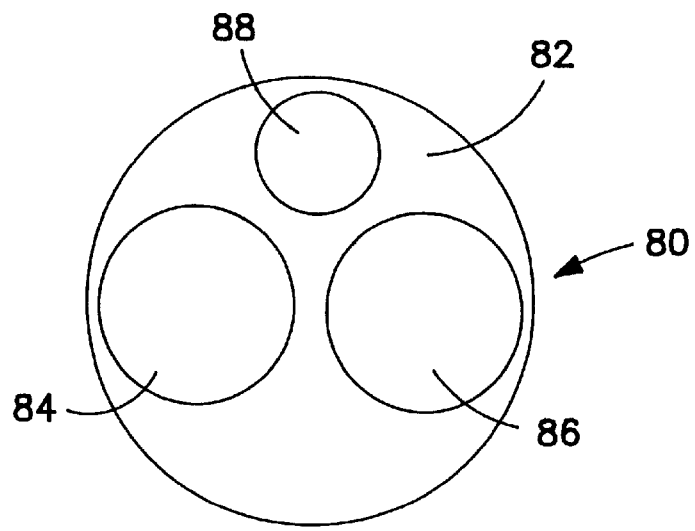
Figure 6:
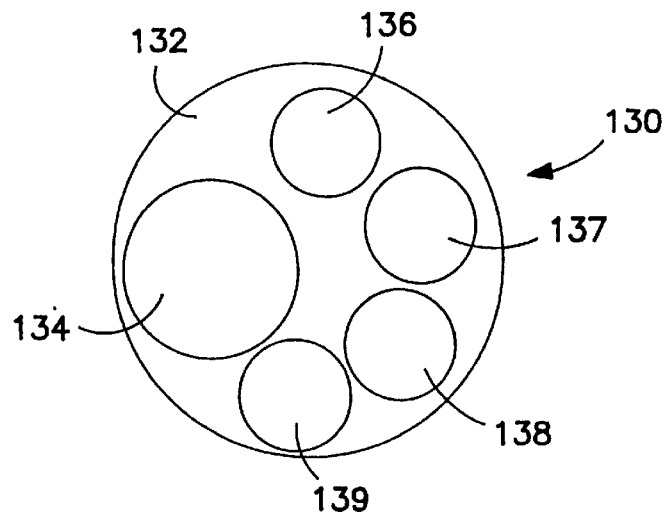
Figure 5:
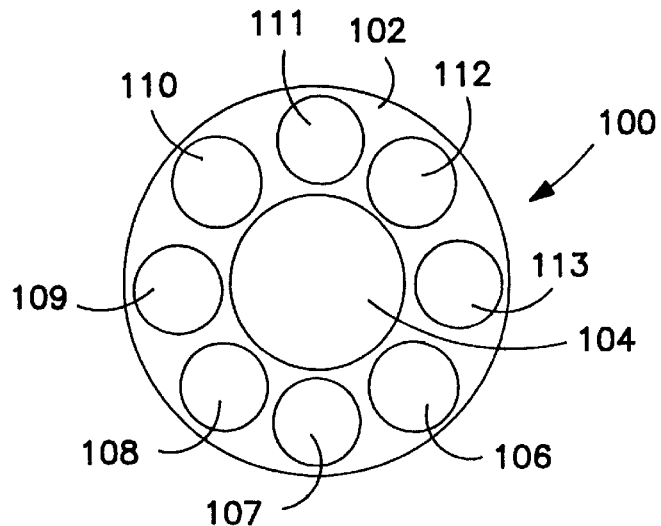
Figure 7:
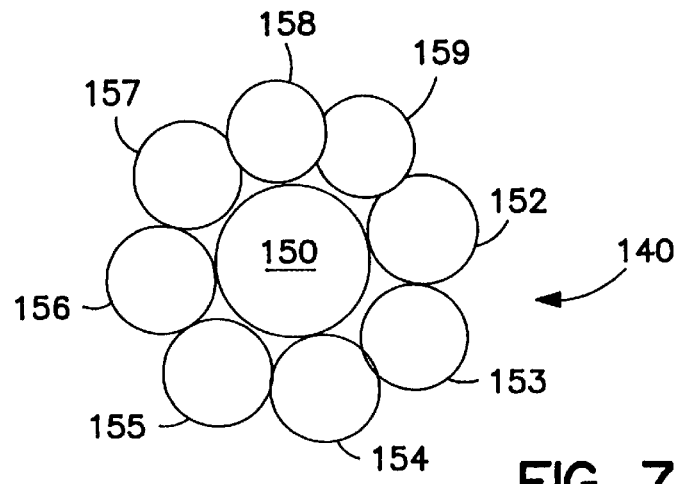

FIGS. 3, 4, 5, 6 and 7 show additional embodiments of the device of the invention. In FIG. 3, device 60 comprises an elongate tubular member 62 with four lumens 64, 66, 68 and 70. In FIG. 4, device 80 comprises an elongate tubular member 82 with three lumens 84, 86 and 88. In FIG. 5, device 100 comprises an elongate tubular member 102 with a large lumen 104 and 8 smaller lumens (106–113) and in FIG. 6, device 130 comprises an elongate tubular member 132 with a large lumen 134 and four smaller lumens 136–139. FIG. 7 is similar to the device shown in FIG. 5, but instead of a single device with 9 lumens, the device 140 is made up of 9 tubular members bundled together, with 1 tubular member (150) having a large lumen and the other tubular members (152–159) having smaller lumens. In these five embodiments, the active agent 18 is usually contained in the larger diameter lumen, which also contains an active agent retainer as shown in FIGS. 1A and 2A. The other lumens are usually empty. However, as noted earlier, they may contain the same or a different active agent as the larger lumen, depending on the condition to be treated.

In order to maintain the integrity of the dose of active agent formulation in the devices described above, the second end of the tubular member may be sealed by means of a cap, plug or other type of seal. In addition, the device may be wrapped in paper, plastic or other material such that it can be easily handled by the patient or care-giver.

The active agent itself may be in liquid, solid, or semisolid form and formed into discrete units. The agents can be soluble and insoluble, charged or uncharged molecules, components of molecular complexes or nonirritating, pharmacologically acceptable salts and may contain additional materials such as binders, coating materials, or stabilizers such that the active agent is formed into one or more discrete units. The discrete units may be designed in a multitude of ways to provide a specific drug delivery profile. One embodiment comprises an active agent that is in particulate form. These particulates are generally between about 50 and 2000 $\mu$m in diameter, usually between about 100–500 $\mu$m in diameter. Where the particulate has an unpleasant taste, the particulate may be taste masked by methods that are well known in the art. The particulates may be designed to provide immediate delivery of the active agent, they may be coated to provide for prolonged release or delayed pulse release of the active agent, or they may be designed to provide for a combination of immediate, pulsed and/or prolonged delivery of active agent. The particulates may be coated with an enteric coating to provide for targeted release of the active agent.

In other embodiments, the active agent may be in liquid form and may be contained within a soft gelatin capsule or within a solid oral dosage form. These dosage forms may include, matrix or other types of tablets, pellets and elongated tablets where the height to diameter ratio exceeds one, capsules, microcapsules, elementary osmotic pumps, such as those described in U.S. Pat. No. 3,845,770, mini osmotic pumps such as those described in U.S. Pat. Nos. 3,995,631, 4,034,756, and 4,111,202, and multichamber osmotic systems referred to as push-pull and push-melt osmotic pumps, such as those described in U.S. Pat. Nos. 4,320,759, 4,327,725, 4,449,983, and 4,765,989 all of which are incorporated herein by reference.

The term "active agent" refers to an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-norprogesterone, norgestrel, norethindrone, norethisterone, norethindrone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captopril, Mandol, guanabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tertatolol, minoxidil, chlordiazepoxide, diazepam, amitriptyline, tetracycline, metronidazole, acyclovir, zidovudine and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and luteinizing hormone.

It is to be understood that more than one active agent may be delivered in a device of this invention, and that the use of the term "agent" in no way excludes the use of two or more such agents. Combination products such as those described, for example, in U.S. Pat. No. 5,256,684 for the treatment of ulcers (tetracycline, metronidazole and bismuth subsalicylate) and for the treatment of AIDS (zidovudine (AZT), a protease inhibitor and 3TC) are particularly suited for delivery using the present invention.

The amount of active agent employed in the delivery device will be that amount necessary to deliver a therapeutically effective amount of the agent to achieve the desired result. In practice, this will vary widely depending upon the particular agent, the severity of the condition, and the desired therapeutic effect. However, the device is generally useful for active agents that must be delivered in fairly large doses of from about 100 mg to 5000 mg, usually in the range of from about 250 mg to about 2500 mg. However, since the devices may also be useful in pediatric patients, doses in the ranges of 25 to 250 mg are also contemplated herein.

Representative materials for forming devices including the active agent formulation chamber, the elongated tubular member, the end caps and tabs, include, without limitation, paper, plastic such as propylene/styrene copolymers, polypropylene, high density polyethylene, low density polyethylene and the like. The devices usually have an outer diameter of between about 4 and 15 mm. The lumens may vary in size according to how many are used, but the drug containing lumens are usually between about 5 and 10 mm and the other lumens are usually between about 1 and 3 mm. The devices are between about 10 and 30 cm in length.

The fluid passing active agent retainer permits the free flow of fluid but prohibits passage of the active agent from the device prior to delivery. Where the retainer comprises a one-way plug or valve, the plug or valve will seal the straw at atmospheric pressure. When suction is applied, fluid will be drawn into each of the lumens. Where the plug in the active agent containing lumen has a density of less than one, it will ascend to the top as the active agent is delivered into the oral cavity. When suction is no longer applied, the plug will remain in the highest position it reached during sipping and will not ascend into the mouth as a result of a constriction or detent at the top of the device.

The drinkable fluid that is used for suspending the active agent formulation by sipping through the active agent formulation chamber is preferably any good-tasting liquid including but not limited to water, juice, milk, soda, coffee, tea etc. Care must be taken to ensure compatibility of the fluid with the active agent formulation.

The above description has been given for ease of understanding only. No unnecessary limitations should be understood therefrom, as modifications will be obvious to those skilled in the art in light of the present disclosure, the drawings and the claims herein.

We claim:

1. A device for administering one or more active agents to a patient, comprising:

an elongate tubular member having a first end and a second end and comprising a first and a second flow path, wherein at least one of said flow paths contains a quantity of discrete units that comprise an active agent, wherein said first end is configured so that said flow paths are adapted for fluid communication with an external fluid, and said second end is configured for oral application of suction by the patient so that the quantity of discrete units is entrained in the fluid that is drawn into the device by the patient.

2. The device of claim 1 wherein, said at least one flow path contains a fluid passing active agent retainer.

3. The device of claim 2 wherein said active agent retainer comprises a grid.

4. The device of claim 2 wherein said active agent retainer comprises a narrowing in the first end of the elongate tubular member.

5. The device of claim 4 wherein the active agent retainer further comprises a plug.

6. The device of claim 1 wherein said discrete units are selected from the group consisting of particulates, oral dosage forms and combinations thereof.

7. The device of claim 1, wherein said discrete units provide for prolonged delivery of the active agent.

8. The device of claim 1 wherein said discrete units provide for immediate delivery of the active agent.

9. The device of claim 1 wherein said discrete units provide for delayed pulsed delivery of said active agent.

10. The device of claim 1, further comprising an end cap concentrically surrounding the second end of the elongated tubular member.

11. The device of claim 1, wherein said active agent is selected from the group consisting of antibiotics, antiviral agents, anepileptics, analgesics, and anti-inflammatory agents, and bronchodilators.

12. The device of claim 1, further comprising a third, fourth and fifth flow path, each of which is adapted for fluid communication with the fluid.

13. The device of claim 12 wherein said at least one flow path has a diameter larger than that of any of the second, third, fourth and fifth flow paths.

14. The device of claim 1 further comprising third and fourth flow paths, adapted for fluid communication with the fluid, having diameters that are smaller than the first and second flow paths.

15. The device of claim 1 further comprising a third flow path adapted for fluid communication with the fluid with a diameter that is smaller than the first and second flow paths.

16. The device of claim 1, further comprising seven additional flow paths, each of which is adapted for fluid communication with the fluid, the first flow path being larger than any of the other flow paths.

17. The device of claim 1, further comprising a quantity of discrete units that comprise a second active agent disposed in the other of said flow paths.

18. A method for administering one or more active agents to a patient comprising:

a. entraining discrete units of an active agent contained in a delivery device in an external fluid that is drawn into the delivery device by the patient and introducing the entrained units into the mouth of the patient; and b. simultaneously introducing a supplemental stream of fluid into the mouth of the patient.

19. The method of claim 18 wherein the supplemental stream of fluid comprises an active agent that is the same as or different from the entrained units of active agent.

20. The method of claim 18 wherein the supplemental stream of fluid does not contain an active agent.

21. The device of claim 1, wherein the quantity of discrete units comprises between 100 and 5000 mg of the active agent.

* * * * *